United States Patent [19]

Brown, deceased

[11] 4,159,281

[45] * Jun. 26, 1979

[54] N-CHLOROTHIO UREAS

[75] Inventor: Melancthon S. Brown, deceased, late of Berkeley, Calif., by Gustave K. Kohn, special administrator

[73] Assignee: Chevron Research Company, San Francisco, Calif.

[*] Notice: The portion of the term of this patent subsequent to Dec. 10, 1991, has been disclaimed.

[21] Appl. No.: 495,948

[22] Filed: Aug. 9, 1974

Related U.S. Application Data

[63] Continuation-in-part of Ser. No. 250,907, May 8, 1972, Pat. No. 3,853,966, which is a continuation-in-part of Ser. No. 88,212, Nov. 9, 1970, Pat. No. 3,755,437, and Ser. No. 189,732, Oct. 15, 1971, abandoned.

[51] Int. Cl.$^2$ .............................. C07C 155/02
[52] U.S. Cl. ................................. 260/545 R
[58] Field of Search ...................... 260/545 R

[56] References Cited

U.S. PATENT DOCUMENTS

| | | | |
|---|---|---|---|
| 3,699,122 | 10/1972 | Kohn | 260/545 |
| 3,853,966 | 12/1974 | Brown | 260/545 |
| 3,857,883 | 12/1974 | Cleveland | 260/545 |

FOREIGN PATENT DOCUMENTS 2045440  3/1972  Fed. Rep. of Germany ........... 260/545

*Primary Examiner*—Robert Gerstl
*Attorney, Agent, or Firm*—Dix A. Newell; T. G. DeJonghe

[57] ABSTRACT

N-chlorothio ureas are produced by the reaction of sulfur dichloride and a urea having at least one hydrogen substituted on a urea nitrogen atom in the presence of an acid acceptor. The N-chlorothio ureas are useful intermediate in the preparation of pesticides.

1 Claim, No Drawings

N-CHLOROTHIO UREAS

CROSS-REFERENCE TO RELATED APPLICATIONS

This application is a continuation-in-part of U.S. Ser. No. 250,907, filed May 8, 1972, now U.S. Pat. No. 3,853,966, which in turn is a continuation-in-part of applications Ser. No. 88,212, filed Nov. 9, 1970, now U.S. Pat. No. 3,755,437, and Ser. No. 189,732, filed Oct. 15, 1971, now abandoned. The disclosures of U.S. Pat. No. 3,755,437 and U.S. Ser. Nos. 250,907 and 189,732 are incorporated by reference.

DESCRIPTION OF THE PRIOR ART

N-chlorothio-N,N',N'-trimethylurea is a known compound which is prepared by the reaction of an N-silylated urea and sulfur dichloride, as disclosed by E. Kuhle, *Synthesis*, 11, 573 (1970). N-chlorothio-N,N'-N'-triorgano-substituted ureas are also disclosed in German Pat. No. 2,045,440, published Mar. 23, 1972.

Processes for producing sulfenyl chloride derivatives of compounds having active hydrogen atoms substituted on nitrogen are also known. E. Kuhle, *Synthesis*, 561 (1970), discloses the preparation of sulfenyl halide derivatives of sulfoamides and amines. U.S. Pat. No. 3,699,122 of Gustave K. Kohn, issued Oct. 17, 1972, discloses the preparation of sulfenyl halide derivatives of amides.

DESCRIPTION OF THE INVENTION

The N-chlorothio ureas of the invention are represented by the formula (I):

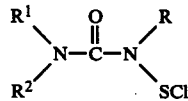

wherein R, $R^1$ and $R^2$ individually are hydrogen or alkyl of 1 to 6 carbon atoms, alkoxy of 1 to 4 carbon atoms, cycloalkyl of 3 to 10 carbon atoms, carbocyclic mononuclear or binuclear aryl of 6 to 12 carbon atoms substituted with up to 2 (0 to 2) substituents selected from fluorine, chlorine, bromine, trifluoromethyl, trichloromethyl, nitro or alkoxy of 1 to 4 carbon atoms.

Representative alkyl groups which R, $R^1$ and $R^2$ may represent include methyl, ethyl, n-propyl, isopropyl, n-butyl, t-butyl, n-pentyl and n-hexyl. The preferred alkyl group is methyl.

Representative alkoxy groups which R, $R^1$ and $R^2$ may represent include methoxy, ethoxy, propoxy and butoxy.

Representative cycloalkyl groups which R, $R^1$ and $R^2$ may represent include monocyclic groups such as cyclopropyl, cyclopentyl, cyclohexyl, 2-methylcyclohexyl, 4-methylcyclohexyl, cycloheptyl, and cyclooctyl; and bicyclic groups such as bicyclo[3.2.0]heptyl, bicyclo[2.2.1]heptyl, bicyclo[3.3.0]octyl, bicyclo[4.2.0]octyl, bicyclo[3.3.0]octyl, and bicyclo[3.2.1]octyl. Cycloalkyl groups preferable are monocyclic groups having 5 to 6 carbon atoms.

Representative hydrocarbyl aryl groups which R, $R^1$ and $R^2$ may represent include phenyl; naphthyl; alkylphenyl of 7 to 10 carbon atoms such as 2-methylphenyl, 3-methylphenyl, 4-ethylphenyl, 2,4-dimethylphenyl, 3,4-dimethylphenyl, 3-secbutylphenyl; and phenylalkyl of 7 to 10 carbon atoms such as benzyl, 3-phenylpropyl, and 4-phenylbutyl.

Representative substituted aryl groups which R, $R^1$ and $R^2$ may represent include phenyl, alkylphenyl or phenylalkyl substituted with 1 to 2 of the same or different substituents on the phenyl ring, such as 2-fluorophenyl, 4-fluorophenyl, 2-chlorophenyl, 3-chlorophenyl, 3,4-dichlorophenyl, 4-trifluoromethylphenyl, 3-chloro-4-bromophenyl, 2-chloro-4-methylphenyl, 2-fluoro-4-methylphenyl, 4-chlorobenzyl, 4-fluorobenzyl, 2-(2-fluorophenyl)ethyl, 4-methoxyphenyl, 4-ethoxyphenyl, 4-methoxy-2-methylphenyl, 4-methoxybenzyl, 2-nitrophenyl, 4-nitrophenyl, 4-nitrobenzyl, 2-methoxy-4-chlorophenyl, and 2-chloro-4-nitrophenyl. Preferred substituted aryl groups are halo-substituted phenyls, especially those having 1 to 2 fluorine or chlorine substituents.

Preferably R is alkyl of 1 to 6 carbon atoms, especially methyl.

Preferably $R^1$ is phenyl or phenyl substituted with 1 to 2 fluorine, chlorine, trifluoromethyl, nitro, alkyl of 1 to 2 carbon atoms, or alkoxy of 1 to 2 carbon atoms.

$R^2$ is preferably hydrogen.

A preferred class of N-chlorothio ureas iof formula (I) is that wherein at least one R, $R^1$ or $R^2$ group is hydrogen. Preferably $R^2$ is hydrogen.

Another preferred class of N-chlorothio ureas is that wherein $R^2$ is hydrogen, R is alkyl of 1 to 6 carbons and $R^1$ is as defined above.

Representative N-chlorothio ureas of formula (I) are:

N-chlorothio urea,
N-chlorothio-N-methyl urea,
N-chlorothio-N,N'-dimethyl urea,
N-chlorothio-N-methyl-N',N'-dimethyl urea,
N-chlorothio-N-methyl-N'-cyclohexyl-N'-methyl urea,
N-chlorothio-N-cyclopentyl-N',N'-diethyl urea,
N-chlorothio-N'-methyl-N,N'-dimethoxy urea,
N-chlorothio-N-(2-norbornyl)-N'-phenyl urea,
N-chlorothio-N-butyl-N'-benzyl urea,
N-chlorothio-N-(2-methylcyclohexyl)-N'-phenyl urea,
N-chlorothio-N-methyl-N'-(2-fluorophenyl) urea,
N-chlorothio-N-methyl-N'-(3,4-dichlorophenyl) urea,
N-chlorothio-N-(3-trifluoromethylphenyl)-N',N'-dimethyl urea,
N-chlorothio-N-phenyl-N',N'-dimethyl urea,
N-chlorothio-N-(3,4-dichlorophenyl)-N'-methoxy-N'-methyl urea,
N-chlorothio-N-(3-chloro-4-bromophenyl)-N'-methoxy-N'-methyl urea,
N-chlorothio-N'-(4-bromophenyl)-N,N'-dimethoxy urea,
N-chlorothio-N-(4-chlorophenyl)-N',N'-dimethyl urea,
N-chlorothio-N-(3,4-dichlorophenyl)-N'-methyl-N-butyl urea,
N-chlorothio-N-(hexahydro-4,7-methanoinden-5-yl)-N',N'-dimethyl urea,
N-chlorothio-N-(2-fluorophenyl)-N'-phenyl-N'-methyl urea,
N-chlorothio-N-(2-fluorophenyl)-N'-benzyl-N'-methyl urea,
N-chlorothio-N-(2-fluorophenyl)-N'-methyl-N'-propyl urea,
N-chlorothio-N-(2-fluorophenyl)-N'-(2-fluorophenyl)-N'-methyl urea,
N-chlorothio-N-methyl-N'-(4-nitrophenyl)-N'-methyl urea, N-chlorothio-N-methyl-N'-(4-methoxyphenyl)-N'-methyl urea,
N-chlorothio-N-(3,4-dichlorophenyl)-N',N'-dimethyl urea,
N-chlorothio-N-(2-fluorophenyl)-N',N'-dimethyl urea,
N-chlorothio-N-(4-methoxybenzyl)-N',N'-dimethyl urea, and
N-chlorothio-N-(2-methylphenyl)-N',N'-dimethyl urea.

The N-chlorothio ureas are prepared in accordance with the following reaction (1):

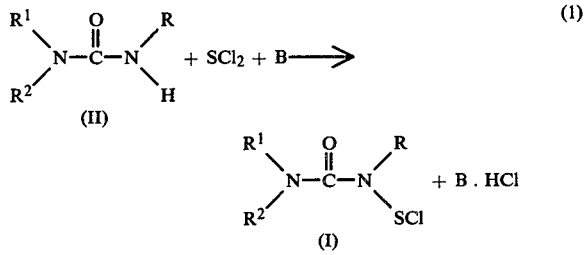

wherein R, R¹ and R² have the same significance as prevousluy defined and R is an acid acceptor.

The acid acceptor is an organic base such as a pyridine compound or a trialkylamine compound. Suitable pyridine compounds are pyridine and pyridine compounds of 6 to 10 carbon atoms and of 1 to 2 alkyl groups such as 2-methylpyridine, 2-ethylpyridine, 3-methylpyridine, 3,5-dimethylpyridine, and 2-butylpyridine. Suitable trialkylamines are those wherein the alkyl group contains individually 1 to 4 carbon atoms, such as trimethylamine, triethylamine, tripropylamine and tributylamine.

Generally, commercially available sulfur dichloride of reasonable purity, e.g., greater than 90-98% purity, is suitably employed. The sulfur dichloride may contain small amounts of an inhibitor such as tributylphosphate or triethylphosphate.

The sulfur dichloride and the urea compound are employed in substantially equimolar amounts, e.g., the molar ratio of sulfur dichloride to the urea compound generally varies from about 1.5:1 to 1:1.5, although molar ratios of sulfur dichloride to the urea compound of 1.4:1 to 1.1:1 are preferred. The molar ratios of acid acceptor to sulfur dichloride are also substantially equimolar, e.g., the molar ratio of acid acceptor to sulfur dichloride varies from about 1.2:1 to 1:1.2, although molar ratios of acid acceptor to suulfur dichloride of 1:1 to 1:1.2 are preferred.

In general, the reaction is accomplished by reacting the urea and the sulfur dichloride in the presence of the acid acceptor compound in an inert diluent. The reaction is suitably conducted by adding the sulfur dichloride to a mixture of the urea and the acid acceptor in an inert diluent. Alternatively, the reaction is conducted by adding a mixture of the urea and acid acceptor to a solution of the sulfur dichloride in an inert diluent. However, the preferred method for conducting the reaction comprises reacting the urea and sulfur dichloride in the presence of a limited amount of free uncomplexed acid acceptor. This is suitably accomplished by the addition of the acid acceptor to a substantially equimolar mixture of the urea and the sulfur dichloride so that the mols of free acid acceptor to the total mols of urea reactant and N-chlorothio urea product is less than 0.2:1, preferably less than 0.1:1, and more preferably less than 0.05:1. In other words, during the course of the reaction between the sulfur dichloride and the urea reactant, there should be at least 5 mols of the urea reactant and the N-chlorothio urea product per mol of acid acceptor which is not complexed with hydrochloric acid. Provided that the reaction is conducted with the restricted amount of acid acceptor indicated above, the contacting of the acid acceptor with the mixture of the urea and the sulfur dichloride can be conducted by a variety of procedures. In one modification, the acid acceptor is added in increments, e.g., dropwise, in an inert diluent, if desired, to a mixture of the urea and sulfur dichloride in an inert diluent. In another modification, the acid acceptor is added continuously to a mixture of the urea and sulfur dichloride is an inert diluent.

Suitable inert diluents for the reaction include alkanes of 5 to 10 carbon atoms, such as hexane, isooctane and decane; aromatic compounds such as benzene and chlorobenzene, oxygenated hydrocarbons such as acyclic alkyl ethers, e.g., dimethoxyethane and dibutyl ether; and cycloalkyl ethers, e.g., dioxane, tetrahydrofuran and tetrahydropyran. Other suitable diluents include nitriles such as acetonitrile and propionitrile, dialkylamides such as dimethylformamide and dialkylsulfoxides such as dimethyolsulfoxide. Preferred diluents are chlorinated hydrocarbons of 1 to 2 carbon atoms, such as methylene dichloride, chloroform, carbon tetrachloride and ethylene dichloride. Generally, the amount of diluent employed ranges from 1 to 50 mols per mol of sulfur dichloride.

The reaction is suitably conducted at a temperature between $-20°$ C. and the boiling point of the diluent, although temperatures between $0°$ C. and $50°$ C. are preferred. The reaction is conducted at or above atmospheric pressure.

It is appreciated, of course, that the N-chlorothio urea product of the invention is formed by the substitution of a hydrogen substituent on a urea nitrogen atom by a sulfenyl chloride group. When the urea reactant has more than one hydrogen substituted on a urea nitrogen, a mixture of monochlorothio derivatives is therefore generally formed (unless the urea reactant is symmetrical, i.e., one R¹ or R² is hydrogen and the other R¹ or R² is the same as R). However, it has been found that when one R, R¹ or R² group is alkyl, the urea compound is preferentially sulfenylated at the nitrogen atom bearing the alkyl group.

The preparation of the N-chlorothio ureas of the invention is illustrated by the following examples:

EXAMPLES

EXAMPLE 1—Preparation of N-chlorothio-N-methyl-N'-2-fluorophenyl urea

A 5.7-g (0.055 mol) sample of sulfur dichloride was added dropwise to a mixture of 8.4 g (0.05 mol) N-methyl-N'-2-fluorophenyl urea and 4.7 g (0.06 mol) pyridine in 50 ml methylene chloride cooled in an ice bath. After the completion of the addition, the pyridine hydrochloride formed during the reaction was filtered. Hexane was added to the filtrate to precipitate additional pyridine hydrochloride, which was removed by filtration. Evaporation of the resulting filtrate gave a clear red oil. The nuclear magnetic resonance (NMR) spectrum of the oil showed an N-methyl singlet at 3.5 ppm (relative to tetramethylsilane). Elemental analysis showed: %S, Calc. 13.6, found 13.6; %Cl, calc. 15.1, found 15.4.

EXAMPLE 2—Preparation of N-chlorothio-N-(3,4-dichlorophenyl)-N',N'-dimethyl urea A 5.7-g (0.055 mol) sample of sulfur dichloride was added dropwise to a mixture of 11.7 g. (0.05 mol) of N-(3,4-dichlorophenyl)-N',N'-dimethyl urea and 4.7 g (0.06 mol) pyridine in 50 ml methylene chloride cooled in an ice bath. After the completion of the addition, the pyridine hydrochloride was filtered. Hexane was added to precipitate additional pyridine hydrochloride, which was removed by filtration. Evaporation of the resulting filtrate gave the product as a clear yellow oil. The NMR spectrum showed an N',N'-dimethyl singlet at 3.0 ppm (relative to tetramethylsilane). Elemental analysis showed: %S, calc. 10.7, found 10.7; %Cl, calc. 35.6, found 35.4; %C, calc. 36.1, found 36.4; %H, calc. 3.0, found 3.2; %N, calc. 9.3, found 8.7.

EXAMPLE 3—Preparation of N-chlorothio-N-methyl-N'-3,4-dichlorophenyl urea

A 9.48-g (0.12 mol) sample of pyridine was added dropwise to a slurry of 21.9 g (0.1 mol) N-methyl-N'-(3,4-dichlorophenyl) urea and 11.3 g (0.11 mol) sulfur dichloride in 100 ml methylene dichloride at 25°–30° C. After the completion of the addition, pyridine hydrochloride was filtered from the reaction mixture. The NMR spectrum of the reaction mixture showed a singlet at 3.5 ppm (relative to tetramethylsilane) for the N-methyl group of the N-chlorothio-N-methyl-N'-3,4-dichlorophenyl urea product.

EXAMPLE 4—Preparation of N-chlorothio-N,N'-dimethyl urea

Pyridine (9.48 g, 0.12 mol) was added dropwise to a solution of 8.8 g (0.1 mol) N,N'-dimethyl urea and 11.3 g 0.11 mol) sulfur dichloride at 25°–30° C. Pyridine hydrochloride was then filtered from the reaction mixture to give a solution of the N-chlorothio urea product in methylene chloride. The NMR spectrum of the product showed a singlet at 3.5 ppm for the N-methyl group and a doublet at 2.95 ppm for the N'-methyl group.

UTILITY

The N-chlorothio urea compounds of the invention are useful intermediates for the preparation of pesticides. Representative types of pesticides which can be prepared from the N-chlorothio urea compounds are illustrated below:

Preparation of N-carboalkoxyalkyldithio urea compounds

The N-chlorothio urea compounds react with mercaptoalkanoate esters to form N-carboalkoxyalkyldithio urea compounds. In terms of the N-chlorothio urea compounds represented by formula (I), the reaction can be depicted by the following equation (2):

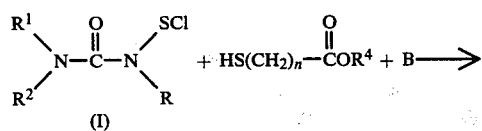

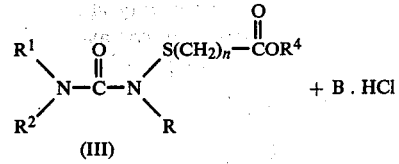

wherein R, $R^1$ and $R^2$ and B have the same significance as previously defined and $R^4$ is alkyl of 1 to 6 carbon atoms and n is 1 or 2.

EXAMPLE 5—Preparation of N-(2-carbomethoxyethyldithio)-N-methyl-N'-(3,4-dichlorophenyl) urea N-chlorothio-N-methyl-N'-(3,4-dichlorophenyl) urea (0.1 mol) in 100 ml methylene chloride was prepared in a manner identical to Example 3. Methyl-3-mercaptopropionate (0.09 mol) and pyridine (7.9 g, 0.1 mol) dissolved in 10 ml methylene chloride was added to the chlorothio urea at 0° C. The reaction was stirred 10 minutes after the addition was completed and the mixture was washed with water, washed with sodium bicarbonate, dried over magnesium sulvate and evaporated under reduced pressure to yield an oil. Chromatography over silica gel (benzene eluent) yielded the product, a dark grey oil. Elemental analysis showed: %S, calc. 17.3, found 17.2; %Cl, calc. 19.2, found 19.6.

By a similar procedure the urea compounds tabulated in Table I were prepared.

The N-carboalkoxydithio urea compounds are, in general, herbicidal in both pre- and post-emergent applications. For pre-emergent control of undesirable vegetation, these ureas will be applied in herbicidal quantities to the locus or environment of said vegetation, e.g., soil infested with seeds and/or seedlings of such vegetation. Such application will inhibit the growth of or kill the seeds, germinating seeds and seedlings. For post-emergent applications, the N-carboalkoxydiethio urea compounds will be applied directly to the foliage and other plant parts. Generally they are effective against weed grasses as well as broadleaved weeds. Some may be selective with respect to type of application and/or type of weed.

Pre- and post-emergent herbicidal tests on the N-carboalkoxyalkyldithio urea compounds prepared above were made using the following methods:

Pre-Emergent Test

An acetone solution of the test urea compound was prepared by mixing 750 mg urea, 220 mg of a nonionic surfactant and 25 ml of acetone. This solution was added to approximately 125 ml of water containing 156 mg of surfactant.

Seeds of the test vegetation were planted in a pot of soil and the urea solution was sprayed uniformly onto the soil surface at a dose of 33 mgc/cm². The pot was watered and placed in a greenhouse. The pot was watered intermittently and was observed for seedling emergence, health of emerging seedlings, etc., for a 3-week period. At the end of this period, the herbicidal effectiveness of the urea was rated based on the physiological observations. A 0-to-100 scale was used, 0 representing no phytotoxicity and 100 representing complete kill.

Post-Emergent Test

The test urea was formulated in the same manner as described above for the pre-emergent test. The concentration of the urea in this formulation was 5000 ppm. This formulation was uniformly sprayed on 2 similar pots of 24-day-old plants (approximately 15 to 25 plants per pot) at a dose of 33 mcg/cm². After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the urea was rated based on these observations. A 0-to-100 scale was used, 0 representing no phytotoxicity and 100 representing complete kill. The results of these tests appear in Table II.

Preparation of Urea Disulfides

The N-chlorothio urea compounds react with sodium iodide to produce bis-urea disulfides of the formula (IV):

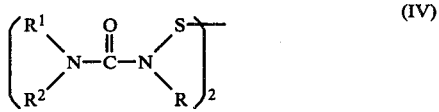

wherein $R^1$, $R^2$ and R have the same significance as previously defined. The preferred R, $R^1$ and $R^2$ groups of the bis-urea disulfides of formula (IV) are the same as the preferred R, $R^1$ or $R^2$ groups of the N-chlorothio ureas of formula (I).

The preparation of a representative bis-urea disulfide is illustrated in the following example:

EXAMPLE 6
Bis-[3-(2-fluorophenyl)-1-methyl-1-ureido]-disulfide

A solution of N-chlorothio-N-methyl-N'-2-fluorophenyl urea in 150 ml methylene dichloride was prepared from 25.2 g (0.15 mol) N-methyl-N'-2-fluorophenyl urea, 17 g (0.16 mol) sulfur dichloride and 14.2 g (0.18 mol) pyridine by a procedure identical to that of Example 1. To the solution of N-chlorothio-N-methyl-N'-2-fluorophenyl urea was then added dropwise a solution of 22 g (0.15 mol) sodium iodide in 45 ml water cooled to about 0° C. in a dry ice/acetone bath. After the addition was completed, the reaction mixture was stirred at 0° C. for about 10-15 minutes. The methylene dichloride layer was separated, washed with sodium thiosulfate solution, washed with sodium bicarbonate solution, washed with water, dried over magnesium sulfate and evaporated under reduced pressure to give 20.2 g of the crude disulfide product as a yellow oil. The crude product was purified by column chromatography on silica (benzene eluent) and crystallized from ether-hexane to give a white solid, m.p. 87°-93° C. Elemental analysis showed: %C, calc. 48.2, found 47.6; %H, calc. 4.0, found 3.9; %N, calc. 14.1, found 13.5; %S, calc. 16.1, found 16.6.

The urea disulfide product was effective as an herbicide for grass and broadleaved weeds.

Preparation of N-dithio ureas

The N-chlorothio urea compounds react with mercaptans to form dithio-substituted ureas. In terms of the N-chlorothio urea compounds of formula (I), the reaction can be depicted by the following equation (3):

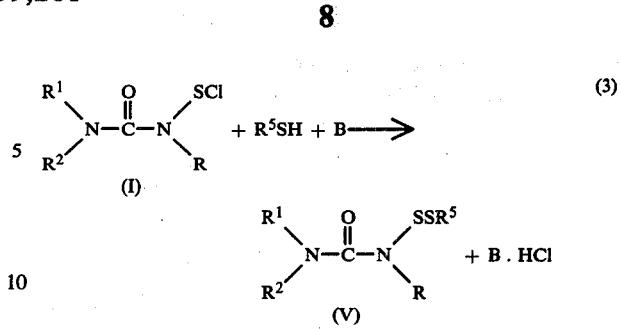

wherein R, $R^1$, $R^2$ and B have the same significance as previously defined and $R^5SH$ is a mercaptan reactant wherein $R^5$ is alkyl, cycloalkyl or aryl R group.

Reaction (3) is carried out be reacting substantially stoichiometric amounts of the reactants in an inert diluent at about 0° to 100° C. The preparation of a representative dithio-substituted urea is illustrated in the following example.

EXAMPLE 7
N-methyl-N-ethyldithio-N'-(3,4-dichlorophenyl) urea

A 9.48-g (0.12 mol) sample of pyridine was added dropwise to a slurry of 21.9 g (0.09 mol) N-methyl-N'-(3,4-dichlorophenyl) urea and 10.3 g (0.1 mol) sulfur dichloride in 100 ml methylene dichloride at 25°-30° C. After the addition was completed, the reaction mixture was stirred for 20 minutes and filtered to give a solution of the chlorothio urea product in methylene dichloride. To the chlorothio urea solution was then added dropwise a solution of 6.2 g ethyl mercaptan and 9.48 g pyridine in 20 ml methylene dichloride at 0° C. After the addition was completed, the reaction mixture was stirred at 0° C. for 10 minutes, washed with water, washed with sodium bicarbonate solution, diluted with benzene and filtered. The filtrate was dried over magnesium sulfate, filtered and evaporated under reduced pressure to give a solid product. The solid product was recrystallized from ether-hexane to give the urea disulfide product, m.p. 108°-109° C. Elemental analysis showed: %S, calc. 20.6, found 20.2; %Cl, calc. 22.8, found 23.1.

By a similar procedure the urea disulfides tabulated in Table III were prepared.

By a procedure identical to that employed for the urea compound of Example 5, the urea disulfides were tested as pre- and post-emergent herbicides. The results are tabulated in Table IV.

Preparation of Aminothio Ureas

The N-chlorothio urea compounds react with primary and secondary amines, amides, anilines and anilides to produce aminothio-substituted ureas according to the following equation (4):

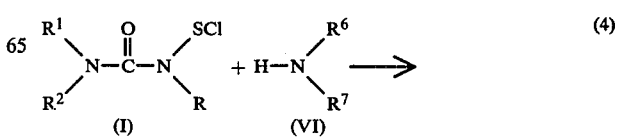

-continued

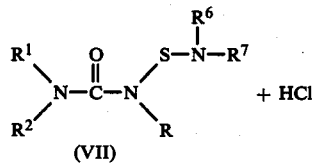

(VII)

wherein R, $R^1$ and $R^2$ have the same significance as previously defined, $R^6$ is alkyl of 1 to 10 carbon atoms, preferably of 1 to 6 carbon atoms, alkanoyl of 2 to 6 carbon atoms, e.g., acetyl, propionyl, etc., or carbocyclic mononuclear or binuclear aryl $R^1$ groups, and $R^7$ is hydrogen or $R^6$. The preferred R, $R^1$ and $R^2$ groups of the aminothio ureas of formula (VI) are the same as the preferred R, $R^1$ or $R^2$ groups of the N-chlorothio ureas of formula (I). $R^7$ is preferably hydrogen or alkanoyl of 2 to 6 carbon atoms. $R^6$ is preferably phenyl, alkylphenyl of 7 to 10 carbon atoms, phenylalkyl of 7 to 10 carbon atoms or phenyl, alkylphenyl, or phenylalkyl substituted with 1 to 2 fluorine, chlorine, bromine, trifluoromethyl, trichloromethyl, nitro, or alkoxy of 1 to 4 carbon atoms.

The preparation of representative aminothio ureas is illustrated by the following examples:

EXAMPLE 8
N-(3,4-dichlorophenylaminothio)-N-methyl-N'-

N-chlorothio-N-methyl-N'-(3,4-dichlorophenyl) urea (0.1 mol) in 100 ml methylene chloride was prepared in a manner identical to Example 3. 3,4-Dichloroaniline (14.5 g, 0.09 mol) and pyridine (9.5 g, 0.09 mol) in 20 ml methylene chloride was added to the chlorothio urea at 0° C. The reaction was stirred 30 minutes at 0° C. after the addition was completed. The resulting reaction solution was washed with water, washed with sodium bicarbonate, dried over magnesium sulfate, and evaporated under reduced pressure to yield an oil. Crystallization from chloroform gave a white solid, m.p. 142°–145° C. Elemental analysis showed: %S, calc. 7.8, found 8.0; %Cl, calc. 34.6, found 34.3.

The product was tested as a pre- and post-emergent herbicide as described heretofore and found to be effective for the control of grass and broad-leaved weeds.

EXAMPLE 9—Preparation of N-methyl-N-(N''-3,4-dichlorophenyl-N''-propionoylaminothio)-N'-(3,4-dichlorophenyl urea N-chloro-N-methyl-N'-(3,4-dichlorophenyl) urea (0.1 mol) in 100 ml methylene chloride was prepared in a manner identical to Example 3. 3,4-Dichlorophenyl-n-propanilide (19.6 g, 0.09 mol) and pyridine (7.9 g, 0.1 mol) were added to the chlorothio urea and the reaction stirred overnight. The resulting mixture was washed with water, washed with sodium bicarbonate, dried over magnesium sulfate, and evaporated under reduced pressure to give a gray solid. Recrystallization from chloroform-hexane gave the product, m.p. 194°–152° C. Elemental analysis showed: %S, calc. 6.9, found 7.0; %Cl, calc. 30.4, found 30.5.

The product was tested as a pre- and post-emergent herbicide as described heretofore and found to be effective for the control of grass and broad-leaved weeds.

Addition to Olefins

The N-chlorothio urea compounds add to olefins to form the corresponding 1,2-addition product as de- picted in the following equation (5) for addition to cyclohexene.

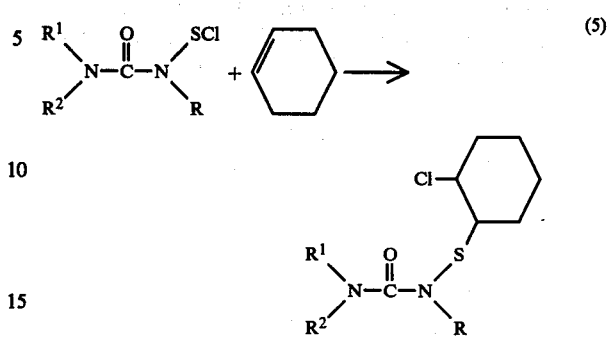

(5)

wherein $R, R^1$ and $R^2$ have the same significance as previously defined.

The invention is conducted by the contacting of substantially equimolar amounts of an olefin and the N-chlorothio urea in an inert solvent at moderate temperatures, e.g., 0° to 50° C.

The preparation of a representative olefin addition product is illustrated by the following example:

EXAMPLE 10
N-methyl-N-(2-chlorocyclohexylthio)-N'-(2-

A 569-g (7.2 mols) sample of pyridine was added over a period of 18 minutes to a mixture of 1008 g (6 mols) of N-methyl-N'-(2-fluorophenyl) urea and 680 g (6.6 mols) sulfur dichloride in 6 ml methylene dichloride cooled to below 30° C. with a dry ice/acetone bath. After the addition was completed, the pyridine hydrochloride salt was filtered. A 443-g (5.4 mol) sample of cyclohexene was then added to the resulting filtrate cooled to 0° C. with a dry ice/acetone bath. After 15 minutes of stirring, the resulting reaction mixture was washed with water, washed with sodium bicarbonate solution, dried over magnesium sulfate and evaporated under reduced pressure to give 1.7 kg of urea product as a yellow oil.

Preparation of 1,2-ethane-bis-urea disulfides

The 1,2-ethane-bis-urea disulfide of the formula (VIII):

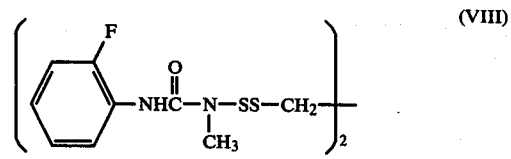

(VIII)

was prepared as follows:

N-chlorothio-N-methyl-N-(2-fluorophenyl) urea (0.1 mol) in 100 ml methylene chloride was prepared in a manner identical to Example 3. 1,2-ethanedithiol (4.2 g, 0.045 mol) and pyridine, 7.9 g (0.1 mol) dissolved in 20 ml methylene chloride were added to the chlorothio urea at 0° C. and the mixture stirred for 10 minutes following the addition. The reaction product was then washed with water, washed with sodium bicarbonate, dried over magnesium sulfate, and evaporated under reduced pressure to yield a white solid. The solid was washed with ether and hexane to give the product, m.p.

92.5°–95° C. Elemental analysis showed: %S, calc. 26.1, found 25.3; %F, calc. 7.8, found 8.0.

The product was effective as a pre- and post-emergent herbicide for grass and broad-leaved weeds.

By a procedure similar to that of the above example, other 1,2-ethane-bis-urea disulfides of the formula (IX):

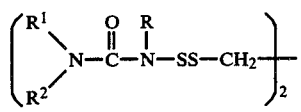

(IX)

wherein R, $R^1$ and $R^2$ have the same significance and preference as defined for the R, $R^1$ and $R^2$ groups of the N-chlorothio ureas of formula (I), can be prepared.

The herbicidal compounds described herein are applied in herbicidally effective amounts to the locus or environment of undesirable vegetation, or directly to the foliage and other plant parts. They can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in chaaracter. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application—i.e., sheltered areas such as greenhouses, as compared to exposed areas such as fields—as well as the desired type of control. Generally, for both pre- and post-emergent control, the herbicidal compounds of the invention are applied at rates of 2 to 60 kg/ha, and the preferred rate is in the range of 5 to 40 kg/ha.

TABLE I

| No. | Compound | Melting Range, °C. | S Calc. | S Found | Halogen Calc. | Halogen Found |
|---|---|---|---|---|---|---|
| (1) | N-(2-carbomethoxyethyldithio)-N-methyl-N'-(3,4-dichlorophenyl) urea | Oil | 17.3 | 17.2 | 19.2 | 19.6 (Cl) |
| (2) | N-(carbomethoxymethyldithio)-N-methyl-N'-(3,4-dichlorophenyl) urea | 94.5–95.5 | 18.0 | 17.6 | 20.0 | 20.0 (Cl) |
| (3) | N-(carbethoxymethyldithio-N-methyl-N'-(3,4-dichlorophenyl) urea | 82–83 | 17.3 | 16.6 | 19.2 | 18.5 (Cl) |
| (4) | N-(carbomethoxymethyldithio)-N-methyl-N'-(3-chloro-4-bromophenyl) urea | 96–97.5 | 16.0 | 15.7 | 5.0 | 5.1 (Br,Cl) |
| (5) | N-(2-carbomethoxyethyldithio)-N-methyl-N'-(2-fluorophenyl) urea | 51–52.5 | 8.8 | 9.0 (N) | — | — |
| (6) | N-(carbomethoxymethyldithio)-N-methyl-N'-(2-fluorophenyl) urea | Oil | 21.1 | 21.2 | 6.3 | 6.2 (F) |
| (7) | N-(2-carbomethoxyethyldithio)-N-methyl-N'-(3-chloro-4-bromophenyl) urea | Oil | 15.5 | 15.2 | 4.8 | 4.8 (Br,Cl) |
| (8) | N-(carbethoxymethyldithio)-N-methyl-N'-(3-chloro-4-bromophenyl) urea | 88.5–91.5 | 15.5 | 15.4 | 4.8 | 4.9 (Br,Cl) |

TABLE II

| | Herbicidal Effectiveness--Pre/Post | | | | | |
|---|---|---|---|---|---|---|
| No. | O | W | C | M | P | L |
| (1) | 45/70 | 100/75 | 90/85 | 100/100 | 100/100 | 100/100 |
| (2) | 95/99 | 100/98 | 100/75 | 100/100 | 100/100 | 100/100 |
| (3) | 100/95 | 100/100 | 100/100 | 100/100 | 100/100 | 100/100 |
| (4) | 55/95 | 80/95 | 85/100 | 90/100 | 100/100 | 100/100 |
| (5) | 100/100 | 100/95 | 100/90 | 100/100 | 100/100 | 100/100 |
| (6) | 95/100 | 100/100 | 100/100 | 100/100 | 100/100 | 100/100 |
| (7) | 40/95 | 100/60 | 100/80 | 100/100 | 100/100 | 100/100 |
| (8) | 60/100 | 100/75 | 100/100 | 100/100 | 100/100 | 100/100 |

O = Wild Oats (*Avenua fatua*)
W = Watergrass (*Echinochloa crusgalli*)
C = Crabgrass (*Digitaria sanguinalis*)
M = Mustard (*Brassica arvensis*)
P = Pigweed (*Amaranthus retroflexus*)
L = Lambsquarter (*Chenopodium album*)

TABLE III

| No. | Compound | Melting Range, °C. | Elemental Analysis | | | |
|---|---|---|---|---|---|---|
| | | | S Calc. | S Found | N Calc. | N Found |
| (9) | N-methyl-N-propyldithio-N'-(3,4-dichlorophenyl) urea | 79 | 19.7 | 19.6 | 21.9 | 21.9 |
| (10) | N-methyl-N-methyldithio-N'-(3,4-dichlorophenyl) urea | 93.5–95 | 21.6 | 21.5 | 23.9 | 24.0 |
| (11) | N-methyl-N-isopropyldithio-N'-(3,4-dichlorophenyl) urea | 103.5–106 | 19.7 | 19.5 | 21.9 | 22.6 |
| (12) | N-methyl-N-n-butyldithio-N'-(3,4-dichlorophenyl) urea | 68–68.5 | 18.9 | 19.0 | 20.9 | 21.0 |
| (13) | N-methyl-N-cyclohexyldithio-N'-(3,4-dichlorophenyl) urea | 97.5–102 | 17.5 | 16.1 | 19.5 | 19.6 |
| (14) | N-methyl-N-p-chlorobenzyldithio-N'-(3,4-dichlorophenyl) urea | 98–103 | 15.7 | 14.2 | 26.1 | 26.2 |
| (15) | N-methyl-N-cyclohexylthio-N'-(2-fluorophenyl) urea | 40–42 | 20.4 | 19.2 | 8.9 | 9.2 |
| (16) | N-methyl-N-propyldithio-N'-(3-chloro-4-bromophenyl) urea | 80–83 | 17.3 | 16.9 | 5.4* | 5.6* |
| (17) | N-methyl-N-n-butyldithio-N'-(3,4-dichlorophenyl) urea | 64–66 | 16.7 | 15.5 | 5.2* | 5.4* |
| (18) | N-methyl-N-methyldithio-N'-(3,4-dichlorophenyl) urea | 99–99.8 | 18.7 | 18.6 | 5.9* | 6.0* |
| (19) | N-methyl-N-methyldithio-N'-(2-fluorophenyl) urea | Oil | 26.0 | 24.3 | 7.7** | 7.4** |
| (20) | N-methyl-N-phenyldithio-N'-methyl urea | 63–64 | 28.1 | 28.0 | — | — |

*Total halogen analysis
**Fluorine analysis

TABLE IV

| No. | O | W | C | M | P | L |
|---|---|---|---|---|---|---|
| * | 25/98 | 50/78 | 95/45 | 100/100 | 75/100 | 98/100 |
| (9) | 80/100 | 87/100 | 93/100 | 100/100 | 98/100 | 100/100 |
| (10) | 35/87 | 35/60 | 55/40 | 100/100 | 100/100 | 100/100 |
| (11) | 30/70 | 50/75 | 87/98 | 100/100 | 99/100 | 95/100 |
| (12) | 45/100 | 70/100 | 93/100 | 95/100 | 95/100 | 98/100 |
| (13) | 20/35 | 50/35 | 100/70 | 100/100 | 100/100 | —/100 |
| (14) | 20/30 | 70/45 | 100/70 | 100/100 | 100/100 | 100/100 |
| (15) | 95/100 | 100/100 | 100/100 | 100/100 | 100/100 | 100/100 |
| (16) | 0/50 | 0/55 | 0/70 | 10/90 | 10/100 | 10/100 |
| (17) | 0/55 | 0/65 | 0/65 | 0/100 | 0/100 | 0/100 |
| (18) | 0/100 | 0/85 | 0/85 | 100/100 | 85/100 | 100/100 |
| (19) | 100/100 | 100/100 | 100/70 | 100/100 | 100/95 | 100/100 |

*N-methyl-N-ethyldithio-N'-(3,4-dichlorophenyl) urea
(O, W, C, M, P and L are as in Table II)

What is claimed is:

1. N-chlorothio-N,N'-dimethyl urea.

* * * * *